US012678093B2

(12) United States Patent
Van Renterghem et al.

(10) Patent No.: US 12,678,093 B2
(45) Date of Patent: Jul. 14, 2026

(54) PENILE TUMESCENCE MEASURING DEVICE

(71) Applicant: Universiteit Hasselt, Hasselt (BE)

(72) Inventors: Koenraad Van Renterghem, Zonhoven (BE); Ronald Thoelen, Zonhoven (BE); Wim Deferme, Hechtel (BE)

(73) Assignee: UNIVERSITEIT HASSELT, Hasselt (BE)

( * ) Notice: Subject to any disclaimer, the term of this patent is extended or adjusted under 35 U.S.C. 154(b) by 1097 days.

(21) Appl. No.: 17/634,674

(22) PCT Filed: Aug. 21, 2020

(86) PCT No.: PCT/EP2020/073501
§ 371 (c)(1),
(2) Date: Feb. 11, 2022

(87) PCT Pub. No.: WO2021/032879
PCT Pub. Date: Feb. 25, 2021

(65) Prior Publication Data
US 2022/0265204 A1 Aug. 25, 2022

(30) Foreign Application Priority Data
Aug. 22, 2019 (EP) ..................................... 19193033

(51) Int. Cl.
*A61B 5/00* (2006.01)
*A61B 5/107* (2006.01)
(52) U.S. Cl.
CPC .......... *A61B 5/4393* (2013.01); *A61B 5/1073* (2013.01); *A61B 5/6813* (2013.01)

(58) Field of Classification Search
CPC .................................................... A61B 5/4393
See application file for complete search history.

(56) References Cited

U.S. PATENT DOCUMENTS

| | | | |
|---|---|---|---|
| 4,911,176 A | 3/1990 | Timm et al. | |
| 6,162,188 A * | 12/2000 | Barnea ................. | A61B 5/4393 600/587 |
| 2018/0206777 A1* | 7/2018 | Yoon ....................... | G16H 50/20 |
| 2021/0251562 A1* | 8/2021 | Jain ......................... | G16H 50/20 |

FOREIGN PATENT DOCUMENTS

| | | | |
|---|---|---|---|
| CN | 105011939 A | 4/2015 | |
| DE | 19733592 A1 * | 9/1998 | ........... A61B 5/4393 |
| WO | 199958052 A1 | 11/1999 | |
| WO | 200112065 A1 | 2/2001 | |

OTHER PUBLICATIONS

International Search Report and Written Opinion mailed Oct. 23, 2020 in reference to co-pending European Application No. PCT/EP2020/073501 filed Aug. 21, 2020.

* cited by examiner

*Primary Examiner* — Thaddeus B Cox
(74) *Attorney, Agent, or Firm* — DINSMORE & SHOHL LLP

(57) ABSTRACT

The present invention is directed to a device for measurement of the rigidity and/or tumescence of a penis during a penile tumescent event. In particular, the device of the present invention comprises axial and/or radial monitoring means for monitoring the axial and/or radial tumescence and/or rigidity of a penis during a penile tumescent event. The present invention further also provides methods for monitoring the axial and/or radial tumescence and rigidity of a penis.

19 Claims, 8 Drawing Sheets

PENILE TUMESCENCE MEASURING DEVICE

CROSS REFERENCES TO RELATED APPLICATIONS

This application is a national-stage application under 35 U.S.C. § 371 of International Application No. PCT/EP2020/073501, filed Aug. 21, 2020, which International Applications claims benefit of priority to European Patent Application No. 19193033.8, filed Aug. 22, 2019.

FIELD OF THE INVENTION

The present invention is directed to a novel device for measurement of the rigidity and/or tumescence of a penis during a penile tumescent event. In particular, with the device of the present invention the axial rigidity and optionally also the radial rigidity can be monitored and measured continuously, and combined in one measurement device. The device of the present invention therefore comprises axial monitoring means for monitoring the axial rigidity of the penis, and optionally radial monitoring means for monitoring the radial rigidity of the penis.

BACKGROUND TO THE INVENTION

When a penis erects, it starts to swell and becomes rigid. Blood fills the erectile tissues and the girth and length of the penis increases. People who have the continuous or intermitted inability to achieve or maintain an erection for satisfactory sexual penetration, suffer from an Erectile Dysfunction (ED). This not only puts a lot of stress on a patient as they may lose confidence in themselves and in their ability to please their partner, but it puts also stress on their (sexual) relationship, social and work activities. In order to treat patients suffering from an ED, a test on Nocturnal Penile Tumescence (NPT) is being performed. NTP is a spontaneous erection of the penis during sleep. All men without physiological ED experience NPT during their sleep. NPT typically occurs during the REM sleep, up to 3-5 times. NPT can be used to differentiate between psychogenic and organic erectile dysfunction.

Prior art measurement techniques for NPT measurements are available, such as for example the Rigiscan®. The Rigiscan® monitoring device enables patients to monitor erections during the night. It has a data collection unit which is attached to the patient's leg, and two loops that are placed at the tip and the base of the penis. This makes it possible to measure both tumescence and rigidity at regular intervals (e.g. every 3 minutes). The Rigiscan® device was the first real non-invasive and standardized tool to evaluate erectile function in males. Though, up till now, no significant improvements on the Rigiscan® have been made so far. From a practical point it is not always as practical as proposed. In a home setting, patients experience a lot of practical problems, such as painful cyclic contraction of the loops, disconnection of the loops; blockage of the engine inside, low quality sleep (REM). Even in a hospital setting the same problems are encountered. In addition, since measurements are only performed at regular intervals and not on a continuous basis, important information can be lost. Consequently, significant and reliable measurements with the Rigiscan® are rather rare meaning that the collected data are not always useful. Further, the Rigiscan® only uses measurements of the radial rigidity at the two locations on the penis, and therefore does not provide all information about the physiology of the full length of the penis.

SUMMARY OF THE INVENTION

The present invention discloses a device for measuring the rigidity and tumescence of a penis. In particular, the device of the present invention is a device for measuring the rigidity and tumescence of a penis and comprises axial monitoring means for monitoring the axial rigidity of the penis and optionally radial monitoring means for monitoring the radial rigidity of the penis. Thus in a first embodiment, the device of the present invention is for measuring one or more physiological parameters of a penis and comprises axial monitoring means for monitoring the axial rigidity of the penis wherein the axial monitoring means each comprise at least two sensors with a different elasticity to each other. In a further embodiment, the device of the present invention further comprises radial monitoring means for monitoring the radial rigidity of the penis wherein said radial monitoring means each comprise at least two sensors with a different elasticity to each other. In another embodiment, the device of the present invention comprises only radial monitoring means for monitoring the radial rigidity of the penis wherein said radial monitoring means each comprise at least two sensors with a different elasticity to each other. The axial monitoring means and/or the radial monitoring means are typically characterized in that they each comprise at least two sensors with a different elasticity to each other. In some aspects, the axial monitoring means and radial monitoring means each comprise at least two sensors with a different elasticity and resistance to each other. In other aspects, the axial monitoring means and/or the radial monitoring means each comprise at least two sensors with a different elasticity but with a similar resistance to each other.

The device of the present invention is thus typically characterized in that it comprises axial monitoring means comprising at least two sensors with a different elasticity to each other. In a further embodiment, the device of the present invention is typically characterized in that it comprises axial monitoring means and radial monitoring means each comprising at least two sensors with a different elasticity to each other. In a particular aspect, said sensors are strain gauge sensors or extensometer sensors.

In a further embodiment, the at least two sensors with a different elasticity to each other of the axial and/or radial monitoring means each comprise one or more semi-conductive means. Thus, in one embodiment, the at least two sensors of the device of the invention each comprise one or more conductive means. In another embodiment, the at least two sensors of the device each comprise one or more semi-conductive means. In still another embodiment, the at least two sensors of the device of the present invention each comprise a mix of one or more semi-conductive and conductive means. In a further embodiment, the semi-conductive or conductive means in the present device can be semi-conductive or conductive wires. In another embodiment, the semi-conductive or conductive means are semi-conductive or conductive tracks.

Thus, in an even further embodiment, the at least two sensors with a different elasticity to each other are strain gauge sensors each comprising one or more semi-conductive means. In another embodiment, the at least two sensors with a different elasticity to each other are semi-conductive or conductive elastic bands.

As already outlined above, the device of the present invention comprises axial monitoring means and optionally also radial monitoring means. In a specific embodiment, the axial monitoring means are configured to be applied in the axial direction of the penis. In another specific embodiment, the radial monitoring means are configured to be applied in the radial direction around the penis. In a further embodiment, the axial monitoring means comprises at least two sensors with a different elasticity to each other and said at least two sensors of the axial monitoring means are applied in the axial direction on the penis. In another further embodiment, the at least two sensors of the radial monitoring means are similar sensors that are applied in the radial direction on the penis.

In still another and different embodiment, the device of the present invention comprises radial monitoring means. Said radial monitoring means are configured to be applied in the radial direction around the penis and they comprise at least two sensors with a different elasticity to each other. Said sensors are applied in the radial direction on the penis.

As said and in the present device, the axial monitoring means comprise at least two sensors with a different elasticity to each other. In a further aspect, the radial monitoring means also comprise at least two sensors with a different elasticity to each other. In a specific embodiment, said at least two sensors with a different elasticity to each other from the axial monitoring means and/or from the radial monitoring means are integrated in a single integrated sensor.

In a further aspect, the at least two sensors with a different elasticity of the axial monitoring means are separated from one another across the width of the penis. In another aspect, the at least two sensors with a different elasticity of the radial monitoring means extend over the length of the penis. Thus, in a particular embodiment, the device of the present invention comprises axial monitoring means that comprise at least two sensors with a different elasticity or resistance to each other that are separated from one another across the width of the penis. In a further embodiment, the device of the present invention comprises axial monitoring means and radial monitoring means, wherein the axial monitoring means comprise at least two sensors with a different elasticity to each other that are separated from one another across the width of the penis, and wherein the radial monitoring means comprise at least two sensors with a different elasticity or resistance to each other that extend over the length of the penis. In an even more specific embodiment, the radial monitoring means are separated from one another across the length of the penis; preferably at least one sensor at the base and at least one sensor at the tip of the penis. In still another embodiment, the present device comprises radial monitoring means that comprise at least two sensors with a different elasticity or resistance to each other. In said embodiment, said at least two sensors are separated from one another across the width of the penis.

In still a further aspect, the axial monitoring means and/or the radial monitoring means further comprise a substrate with an elasticity that does not exert any resistance or only provides a minimal resistance to the erection of the penis. Thus, in one embodiment, the axial monitoring means further comprises a substrate with an elasticity that does not exert any resistance or only provides a minimal resistance to the erection of the penis. In another embodiment, the radial monitoring means further comprises a substrate with an elasticity that does not exert any resistance or only provides a minimal resistance to the erection of the penis. In yet another embodiment, the axial monitoring means and the radial monitoring means both comprise a substrate with an elasticity that does not exert any resistance or only provides a minimal resistance to the erection of the penis. In a specific embodiment, the substrate of the axial monitoring means and the substrate of the radial monitoring means is the same substrate and forms a common substrate. In yet another aspect, the at least two sensors of the axial and/or radial monitoring means are attached to the substrate. In a more specific embodiment, the at least two sensors are attached to the substrate at the ends of the sensors. In an even more specific embodiment, the at least two sensors are semi-conductive or conductive elastic bands, for example stretchable tracks, attached to the substrate at the ends of said semi-conductive or conductive elastic bands.

In some aspects of the invention, the substrate of the device comprises mounting means to place the device on the penis. More specifically, said mounting means may comprise one or more adhesive points to stick the device to the penis.

As already said, in some aspects of the invention, the at least two sensors of the axial monitoring means are attached to a substrate. In a preferred embodiment, said substrate is a common substrate to which the axial monitoring means are attached. In a further aspect, the substrate is a sheet, in particular a quadrangle to which the axial monitoring means are attached and wherein the adhesive points are at the extremities of the substrate; in particular at the corners of the substrate. In an even further aspect, the at least two sensors of the axial and radial monitoring means are attached to the substrate. In a preferred embodiment, said substrate is a common substrate to which both the axial and radial monitoring means are attached. In an even further aspect, the common substrate is a sheet, in particular a quadrangle. In still a further aspect, the common substrate is a quadrangle to which both the axial and radial monitoring means are attached and wherein the adhesive points are at the extremities of the substrate; in particular at the corners of the substrate. In still another embodiment, the substrate can be fully adhesive, such as for example a medical skin tape.

In a further aspect, the device according to all its different embodiments further comprises transducer means configured to transduce the changes in physiological parameters of the penis into electrical signals. Said physiological parameters are selected from rigidity of the penis, tumescence of the penis, hardness of the penis, diameter of the penis, growth of the penis, duration of the erection, swelling time of the penis. In a preferred embodiment, said physiological parameters are selected from hardness of the penis and diameter of the penis.

In another further aspect, the device according to all its different embodiments further comprises recording means configured to record the electrical signals from the transducer means. In still another further aspect, the device comprises control means being configured to be electrically connected to the transducer means for providing control to said transducer means.

In another aspect, the device of the present invention further comprises interface means configured to provide communication with peripheral equipment. In one embodiment, said communication is a wire-less communication. In another embodiment, said communication is a wired communication. In still another embodiment, the communication with peripheral equipment can be a combination of both wire-less and wired communication.

In another aspect, the present application provides a method for measuring the rigidity and/or tumescence of a penis during a penile tumescent event. In particular, said method is a non-diagnostic method which can be executed by a non-medically trained person, for example by the patient itself. In said method, only the rigidity and/or tumescence of the penis is measured and data are stored on data storage means. Further analysis of said data in order to evaluate the penile tumescence event by a medically trained person is not included in said method. The method comprises measuring the axial rigidity and/or tumescence of the penis and calculating the overall rigidity and/or tumescence of the penis based on the measurements of the axial rigidity and/or tumescence of the penis. In a further aspect, the method is a non-diagnostic method comprising measuring the axial rigidity and/or tumescence of the penis, measuring the radial rigidity and/or tumescence of the penis, calculating the overall rigidity and/or tumescence of the penis based on the measurements of the axial and radial rigidity and/or tumescence of the penis. In still another embodiment, the application provides a method for measuring the rigidity and/or tumescence of a penis during a penile tumescent event wherein the radial rigidity and/or tumescence of the penis is measured and the overall rigidity and/or tumescence of the penis is then automatically calculated based on the measurements of the radial rigidity and/or tumescence of the penis. In a further embodiment, the method is a non-diagnostic method comprising measuring the radial rigidity and/or tumescence of the penis.

In another aspect, a non-diagnostic method for monitoring one or physiological parameters of a penis during a penile tumescent event with a device according to any one of the disclosed embodiments is provided. Said method comprises positioning the axial monitoring means on the penis, optionally positioning the radial monitoring means around the penis, measuring the resistance of the at least two sensors in the axial monitoring means and optionally also in the radial monitoring means during a period of time, monitoring the one or more physiological parameters by measuring the changes in resistance of the at least two sensors in the axial monitoring means over said period of time, optionally in combination with the changes in resistance of the at least two sensors in the radial monitoring means over said period of time.

In another embodiment, a non-diagnostic method for monitoring one or physiological parameters of a penis during a penile tumescent event with a device according to any one of the disclosed embodiments is provided. Said method comprises positioning the radial monitoring means on the penis, measuring the resistance of the at least two sensors in the radial monitoring means during a period of time, monitoring the one or more physiological parameters by measuring the changes in resistance of the at least two sensors in the radial monitoring means over said period of time.

Said one or more physiological parameters of the penis are further selected from rigidity of the penis, tumescence of the penis, hardness of the penis, diameter of the penis, growth of the penis, duration of the erection, swelling time of the penis. In a preferred embodiment, said physiological parameters are selected from hardness of the penis and diameter of the penis. In another preferred embodiment, said physiological parameters are selected from the rigidity of the penis and the tumescence of the penis. Thus, in a particular embodiment, the present invention provides a non-diagnostic method for monitoring the rigidity and/or tumescence of a penis during a penile tumescence event with a device according to any of the described embodiments. Said method comprises positioning the axial monitoring means on the penis, optionally positioning the radial monitoring means around the penis, measuring the resistance of the at least two sensors in the axial monitoring means during a period of time and optionally in the radial monitoring means, monitoring the rigidity and/or tumescence of the penis by measuring the changes in resistance of the at least two sensors in the axial monitoring means optionally in combination with the radial monitoring means over said period of time.

In all different embodiments of said methods, measuring the changes in resistance of the at least two sensors in each of the monitoring means can be done using a mathematical calculation, for example by measuring the ratio between both resistances. This can be done for the axial monitoring means, and optionally also in combination with the radial monitoring means.

The present invention can further be described in the following embodiments:

1. A device for measuring one or more physiological parameters of a penis, said device comprising axial monitoring means for monitoring the axial rigidity of the penis wherein the axial monitoring means each comprise at least two sensors with a different elasticity to each other.

2. The device of embodiment 1, further comprising radial monitoring means for monitoring the radial rigidity of the penis wherein said radial monitoring means each comprise at least two sensors with a different elasticity to each other.

3. The device of embodiment 1 or 2, wherein the at least two sensors each comprise one or more semi-conductive or conductive means; preferably one or more stretchable semi-conductive or conductive means.

4. The device of any of the preceding embodiments, wherein the one or more conductive means are semi-conductive or conductive wires or tracks.

5. The device of any one of the preceding embodiments wherein the axial monitoring means are configured to be applied in the axial direction on the penis.

6. The device of any one of the preceding embodiments 2 to 5, wherein the radial monitoring means are configured to be applied in the radial direction around the penis.

7. The device of any one of the preceding embodiments 2 to 6 wherein the radial monitoring means are configured to be applied in the radial direction around the penis, and wherein the axial monitoring means are configured to be applied in the axial direction on the penis.

8. The device of any one of the preceding embodiments wherein the at least two sensors with a different elasticity to each other are integrated in a single integrated sensor.

9. The device of any one of the preceding embodiments, wherein the at least two sensors of the axial monitoring means are separated from one another across the width of the penis.

10. The device of any one of the preceding embodiments 2 to 9, wherein the at least two sensors of the radial monitoring means extend over the length of the penis.

11. The device of any one of the preceding embodiments 2 to 10, wherein the at least two sensors of the radial monitoring means are separated from one another across the length of the penis; preferably at least one sensor at the base of the penis and at least one sensor at the tip of the penis.

12. The device of any one of the preceding embodiments, wherein the at least two sensors of the axial monitoring means extend over the width of the penis.

13. The device of any of the preceding embodiments, wherein the at least two sensors of the axial monitoring means are semi-conductive or conductive elastic bands, for example semi-conductive or conductive stretchable electrodes.

14. The device of any of the preceding embodiments 2 to 13, wherein the at least two sensors of the radial monitoring means are semi-conductive or conductive elastic bands, for example semi-conductive or conductive stretchable electrodes.

15. The device of any of the preceding embodiments, wherein the axial monitoring means and/or the radial monitoring means further comprise a substrate with an elasticity that does not exert or exerts only a minimal resistance to the erection of the penis.

16. The device of embodiment 15, wherein the at least two sensors of the respectively axial and radial monitoring means are attached to the substrate.

17. The device of embodiment 16, wherein the at least two sensors are attached to the substrate at the ends of the sensors.

18. The device according to any one of the embodiments 15 to 17, wherein the substrate of the axial monitoring means and/or the radial monitoring means is a common substrate.

19. The device according to any one of the embodiments 15 to 18, wherein the substrate comprises mounting means to place the device on the penis.

20. The device according to embodiment 19, wherein the mounting means consist of one or more adhesive points to stick the device to the penis.

21. The device according to embodiment 20, wherein the common substrate is a sheet; in particular a quadrangle, with the one or more adhesive points at the extremities; in particular at the corners of said sheet.

22. The device according to any one of the preceding embodiments, further comprising transducer means configured to transduce the changes in one or more physiological parameters of the penis into electrical signals.

23. The device according to embodiment 22, wherein the one or more physiological parameters are selected from rigidity of the penis, tumescence of the penis, hardness of the penis, diameter of the penis, growth of the penis, duration of the erection, swelling time of the penis; preferably selected from hardness of the penis, diameter of the penis, rigidity of the penis and tumescence of the penis.

24. The device according to any one of the preceding embodiments, further comprising recording means configured to record the electrical signals from the transducer means.

25. The device according to any one of the preceding embodiments, further comprising control means being configured to be electrically connected to the transducer means for providing control to said transducer means.

26. The device according to any one of the preceding embodiments, further comprising interface means configured to provide communication with peripheral equipment.

27. The device according to embodiment 26 wherein the communication with peripheral equipment is a wire-less communication.

28. The device according to embodiment 26 wherein the communication with peripheral equipment is a wired communication.

29. A non-diagnostic method for measuring the rigidity and/or tumescence of a penis during a penile tumescent event, said method comprising:
    measuring the axial rigidity and/or tumescence of the penis;
    optionally measuring the radial rigidity and/or tumescence of the penis;
    calculating the overall rigidity and/or tumescence of the penis based on the measurements of the axial rigidity and/or tumescence of the penis optionally in combination with the measurements of the radial rigidity and/or tumescence of the penis.

30. A non-diagnostic method for monitoring one or more physiological parameters of a penis during a penile tumescent event with a device according to any one of the embodiments 1 to 28, said method comprising:
    positioning the axial monitoring means on the penis;
    optionally positioning the radial monitoring means around the penis;
    measuring the resistance of the at least two sensors in the axial monitoring means during a period of time;
    optionally measuring the resistance of the at least two sensors in the radial monitoring means during a period of time;
    monitoring the one or more physiological parameters by measuring the changes in resistance of the at least two sensors in the axial monitoring means over said period of time, optionally combined with the changes in resistance of the at least two sensors in the radial monitoring means over said period of time.

31. The non-diagnostic method of embodiment 30 wherein the one or more physiological parameters are selected from rigidity of the penis, tumescence of the penis, hardness of the penis, diameter of the penis, growth of the penis, duration of the erection, swelling time of the penis.

32. The non-diagnostic method of embodiment 30 or 31, further comprising generating the ratio of the resistance between the at least two sensors in the axial monitoring means and monitoring the one or more physiological parameters of the penis based on the ratio of the resistance between the at least two sensors in the axial monitoring means.

33. The non-diagnostic method of embodiment 32, further comprising generating the ratio of the resistance between the at least two sensors in the radial monitoring means and monitoring the one or more physiological parameters of the penis based on the ratio of the resistance between the at least two sensors in the radial monitoring means.

34. The method of any of the embodiments 29 to 33 further comprising measuring or evaluating other health parameters of the male subject.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

(FIG. 1A) Axial monitoring means attached on the substrate; (FIG. 1B) radial and axial monitoring means attached on the substrate of the device according to an embodiment of the invention. (FIG. 1C) In a particular embodiment, the device according to the invention comprises a peripheral equipment, such as a sensor node and a wired communication between the monitoring means of the device and said peripheral equipment.

DETAILED DESCRIPTION OF THE INVENTION

Figure 1A:
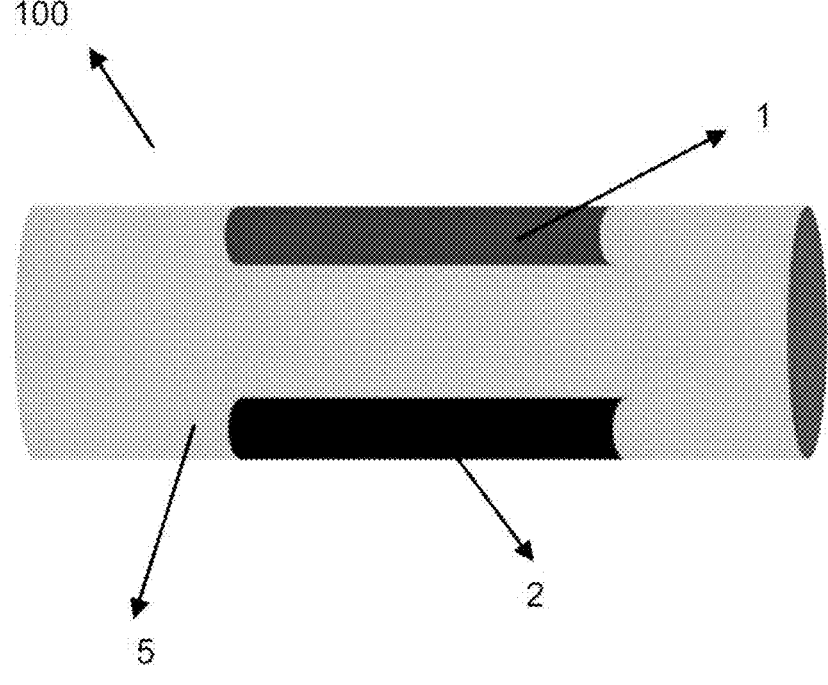
FIGS. 1A-1C: Device for measuring the rigidity and tumescence of a penis according to an embodiment of the invention. The device according to the invention comprising axial monitoring means (1, 2) for monitoring the axial rigidity of the penis and optionally radial monitoring means (3, 4) for monitoring the radial rigidity of the penis. The device may further comprise a substrate (5) onto which the monitoring means are attached.

The present invention provides a device (100) for measuring the rigidity and tumescence of a penis. Said device comprises axial monitoring means (1, 2) for monitoring the axial rigidity of the penis and optionally also radial monitoring means (3, 4) for monitoring the radial rigidity of the penis, wherein the axial monitoring means and optionally the radial monitoring means each comprise at least two sensors with a different elasticity to each other (FIG. 1). In a specific embodiment, the axial monitoring means and the radial monitoring means are each at least two sensors with a different elasticity to each other.

In a further aspect, the different sensors of the device of the present invention each comprise one or more semi-conductive or conductive means, such as for example semi-conductive or conductive wires or tracks.

The device of the present invention is typically characterized in that it allows the monitoring of the axial rigidity and tumescence of the penis. Therefore, the axial monitoring means are configured to be applied in the axial direction on the penis. Whereas in the device currently described in the prior art only radial measurements are executed, the device of the present invention is typically characterized by its axial measurements. The invention therefore not only provides a user-friendly device but also introduces new possibilities such as measuring the speed at which an erection occurs and evaluating the erection in the total length of the penis and not only at one location in the penis. Further, the device of the present invention allows monitoring of the physiological parameters of the penis on a continuous basis and not only at regular intervals. To this end, the device comprises axial monitoring means. In a further embodiment, the axial monitoring means are configured to be applied in the axial direction on the penis.

In another embodiment, the device of the present invention is typically characterized in that it allows the monitoring of both the axial and radial rigidity and tumescence of the penis. Therefore, in this embodiment, both axial and radial monitoring means are present in the device, which allows the simultaneous monitoring of both the axial and radial rigidity and tumescence of the penis. The device according to this embodiment of the present invention is thus typically characterized in that it allows monitoring of the penile rigidity wherein a distinction is made between axial and radial rigidity, and wherein both types of rigidity are combined in the final measurement of the penile rigidity and tumescence. The combination of monitoring both axial rigidity and radial rigidity of the penis in one single device not only provides a user-friendly device but also introduces new possibilities such functional analysis of the penis using both axial and radial rigidity data.

In still another further embodiment, the radial monitoring means are configured to be applied in the radial direction around the penis. Thus, in an embodiment, the device of the present invention comprises axial monitoring means that are configured to be applied in the axial direction on the penis and radial monitoring means that are configured to be applied in the radial direction around the penis.

Figure 2:
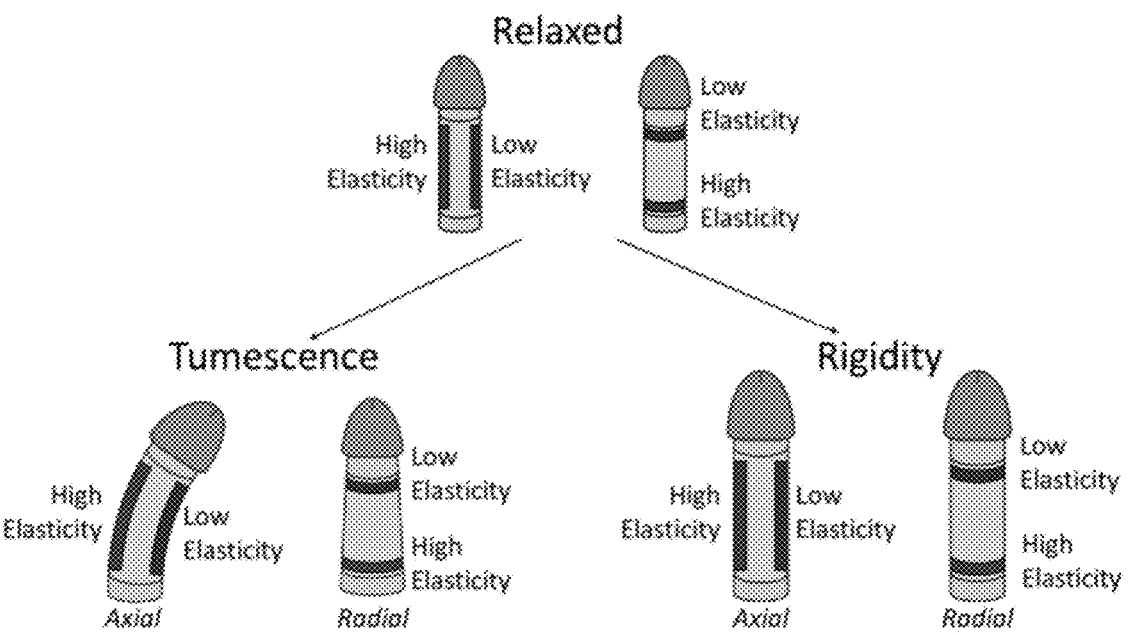
FIG. 2: Measurement principle to measure tumescence and rigidity with a device according to the invention.

As can be observed in FIG. 2, in one embodiment of the invention, the at least two sensors with different elasticity of the axial monitoring means are separated from one another across the width of the penis. In another embodiment, the at least two sensors of the radial monitoring means extend over the length of the penis.

Typical for the invention is also that the at least two sensors of the radial and/or axial monitoring means have a different elasticity to each other. In a further embodiment, said sensors comprise conductive or semi-conductive means that deform when the sensors are subjected to an external applied force, i.e. when the erection of the penis occurs. As deformation of the sensors takes place, the resistance value of the sensor changes linearly with the exerted force. The at least two sensors further have a certain operation range. Within the operation range, the resistance value will change linearly with the applied external force. When the senor is at the end of its operation range, the conductive wire is completely stretched. The resistance value will no longer change with an increasing deformation and further stretching of the sensor will result in damage.

The at least two sensors of the axial and/or radial monitoring means have thus a different elasticity to each other. For each type of rigidity (axial or radial), at least two sensors, such as sensor strips, are used, each with a different elasticity. One sensor has a high elasticity and will deform as the penis swells due to blood filling of the erectile tissue (tumescence). The other sensor has a lower elasticity and will deform as the penis gets more rigid (rigidity). When the sensors are in their initial state, no force is exerted on the sensors and no deformation takes place. The resistance values will not change over time, and hence also to ratio of both the axial and radial resistance values will be constant.

Figure 3:
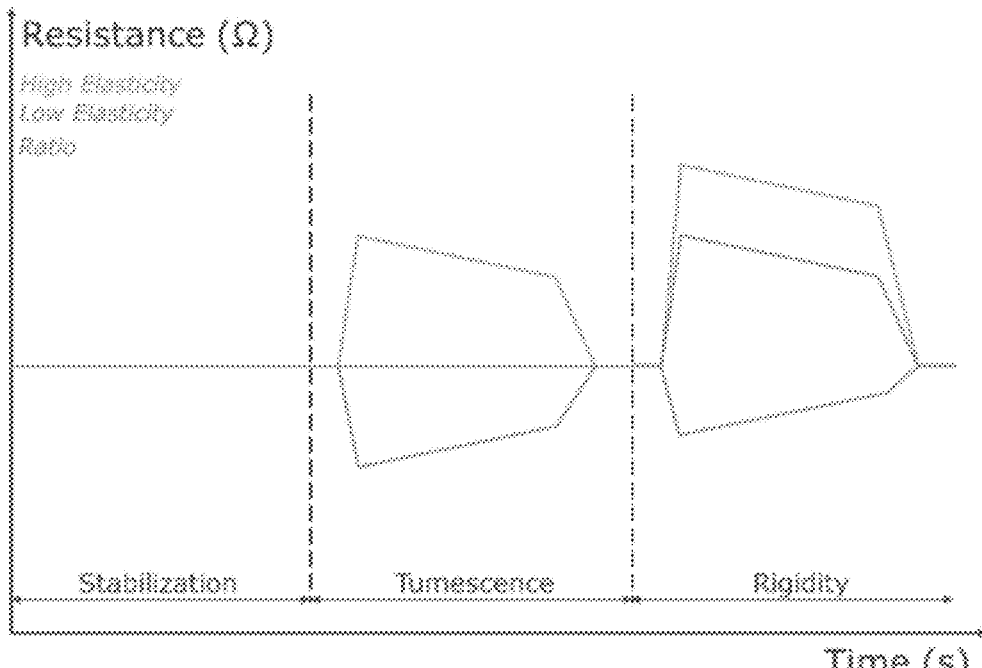
FIG. 3: Expected time measurement when measuring tumescence and rigidity.

When the penile erection starts, a force will be exerted and the sensors of both the axial and radial monitoring means will start to deform. As both sensors have a different elasticity, the deformation of the sensors with the highest elasticity will be greater than the deformation of the sensor with the lowest elasticity (also see FIG. 2). Due to the deformation, a change in resistance values takes will take place. When the penis swells, but is still not rigid, only the sensor with the highest elasticity will deform, and tumescence can be measured. When both sensors are deforming, this indicates that the penis is now also getting rigid, and then penile rigidity can be determined by calculating the ratio of these values. For example, FIG. 3 shows a measurement over time. When the penis swells but does not get rigid, only the sensor with the highest elasticity will deform resulting in measuring tumescence. When the penis becomes rigid, both sensors will deform and penile rigidity can be measured.

The sensors and/or the semi-conductive or conductive means of the device of the present invention can be of any material, for example textile, rubber, plastic or nylon.

The present invention is now further illustrated using the following figures.

Figure 1B:
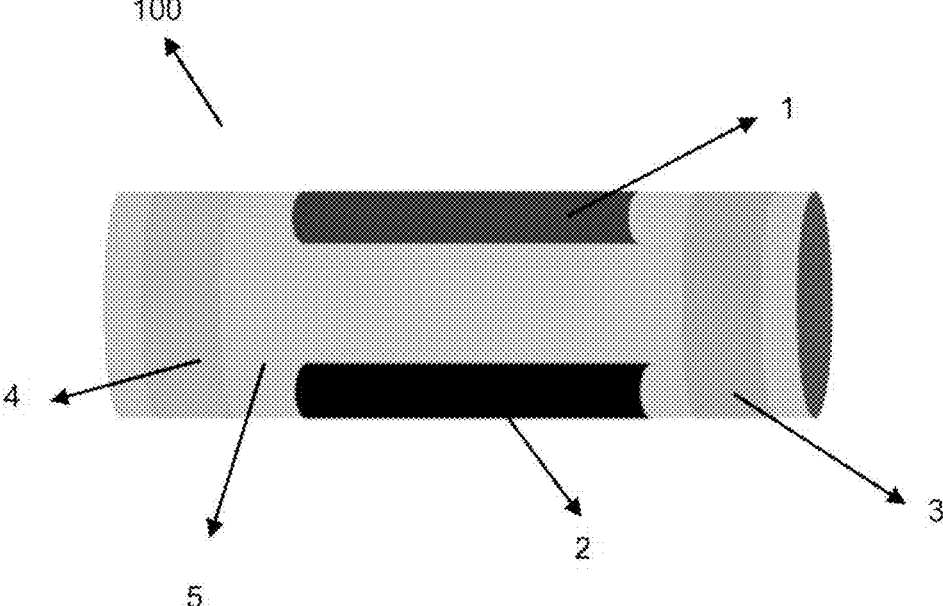
Figure 1C:
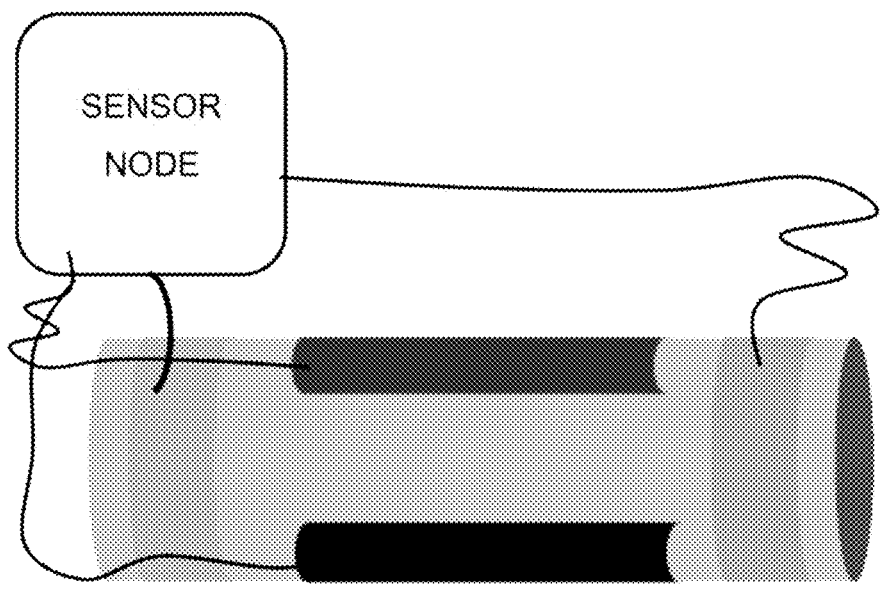

FIGS. 1A-1C represent the device according to some embodiments of the invention. In one of the embodiments (FIG. 1A), the device of the present invention comprises axial monitoring means (1, 2) for monitoring the axial rigidity of the penis wherein said monitoring means are attached to a substrate. In another embodiment (FIG. 1B) the device comprises axial monitoring means (1, 2) for monitoring the axial rigidity of the penis and radial monitoring means (3, 4) for monitoring the radial rigidity of the penis, and wherein said axial and radial monitoring means are attached to a substrate.

In a further aspect, the device of the present invention comprises transducer means configured to transduce the changes in hardness and diameter of the penis into electrical signals.

The device of the present invention may further comprise control means that are configured to be electrically connected to the transducer means for providing control to said transducer means.

The device further also comprises a peripheral equipment, such as a sensor node and a wired or wireless communication between the monitoring means of the device and the peripheral equipment. In a further embodiment, the sensor node can be a home-made sensor node or a commercially available sensor node, such as for example a Byteflies® node.

In another embodiment, the wired communication between the monitoring means and the peripheral equipment is made via any suitable connection that allows the measurement of changes in resistance, either directly or via Wheatstone bridge circuit. In still another and specific embodiment, the connection between the monitoring means and the peripheral equipment such as the sensor node is made via a flexible printed circuit board. In still another embodiment, the communication between the monitoring means and the peripheral equipment is wireless.

In still another aspect, the device further comprises interface means being configured to provide communication with peripheral equipment.

The device according to the present invention is thus configured to be in communication with a peripheral equipment. Said communication can be a wire-less communication or a wired communication, such as described in FIG. 1C.

Figure 4:
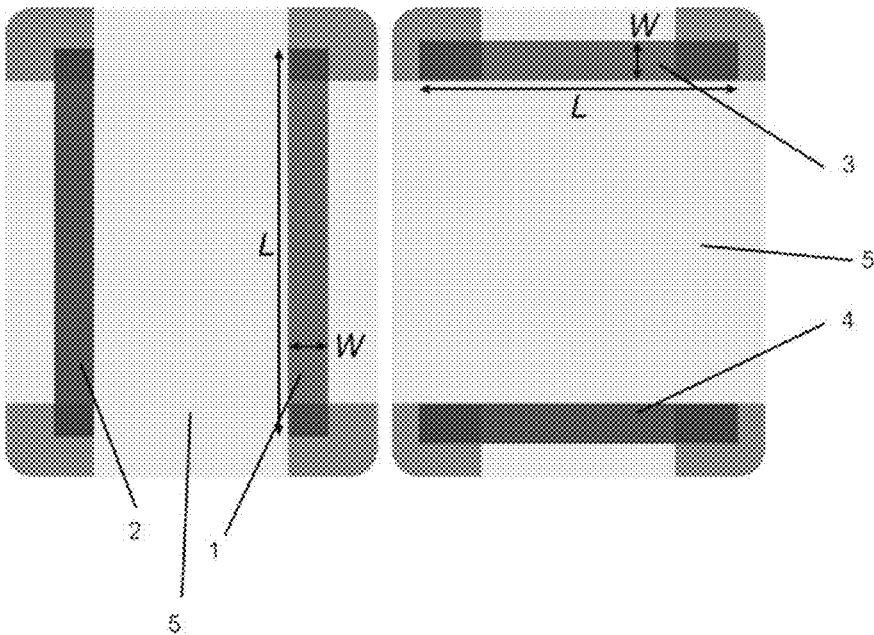
FIG. 4: Fold out substrate and axial and radial monitoring means of the device as displayed in FIGS. 1A and 1B. In this embodiment, the monitoring means are textile strips that are attached to the substrate at their ends. W: width; L: length FIG. 5 Artificial penis as used in the experiments for performing axial and/or radial measurements in a test setting.

In a particular embodiment, and as displayed in FIG. 4, the substrate of the device is a sheet, in particular a quadrangle. In a further embodiment, and as also described in FIG. 4, the radial monitoring means and/or the axial monitoring means are attached to the substrate with their ends.

In a particular aspect, the device according to the invention thus comprises:

axial monitoring means for monitoring the axial rigidity of the penis;

optionally radial monitoring means for monitoring the radial rigidity of the penis;

a substrate;

transducer means configured to transduce the changes in hardness and diameter of the penis into electrical signals;

recording means configured to record the electrical signals from the transducer means;

control means being configured to be electrically connected to the transducer means for providing control to said transducer means;

interface means configured to provide communication with peripheral equipment;

wherein the axial monitoring means and optionally the radial monitoring means each comprise at least two sensors with a different elasticity or resistance to each other.

The present invention also provides a method for measuring the rigidity and/or tumescence of a penis during a penile tumescent event. In a particular aspect, said method is a non-diagnostic method that can be executed by a non-medically trained person, for example by the subject or patient itself. Said method comprises measuring the axial rigidity and/or tumescence of the penis, optionally measuring the radial rigidity and/or tumescence of the penis, calculating the overall rigidity and/or tumescence of the penis based on the measurements of the axial rigidity and/or tumescence of the penis and optionally the radial rigidity and/or tumescence of the penis.

In another embodiment, the invention provides a method for measuring one or more physiological parameters of a penis during a penile tumescent event with a device according to any one of the embodiments of this invention. In a further aspect, this method is a non-diagnostic method, in particular a non-diagnostic method that can be executed by a non-medically trained person, for example by the patient or subject itself. Said method comprising positioning the axial monitoring means on the penis, optionally positioning the radial monitoring means around the penis, measuring the resistance of the at least two sensors in the axial monitoring means during a period of time and optionally in the radial monitoring means, monitoring of the one or more physiological parameters by measuring the changes in resistance of the at least two sensors in said monitoring means over said period of time. In a further embodiment, said method comprises calculating the ratio of the resistance between the at least two sensors in the axial monitoring means, and measuring the one or more physiological parameters of the penis based on the ratio of the resistance between the at least two sensors in the axial monitoring means. In a further embodiment, the ratio of the resistance between the at least two sensors in the radial monitoring means is calculated and used in combination with the ratio of the axial monitoring means to measure the one or more physiological parameters of the penis. In a further aspect, said one or more physiological parameters of the penis are further selected from rigidity of the penis, tumescence of the penis, hardness of the penis, diameter of the penis, growth of the penis, duration of the erection, swelling time of the penis. In a preferred embodiment, said physiological parameters are selected from hardness of the penis and diameter of the penis. In another preferred embodiment, said physiological parameters are selected from the rigidity of the penis and the tumescence of the penis.

EXAMPLES

A. Measuring Device

The measuring device used in the present examples represents a possible embodiment of a device according to the present invention. The device comprises axial or radial monitoring means that each comprise two sensors with a different elasticity to each other. In the device as used herein, the sensors are textile sensors that are used to monitor the penile rigidity. They consist of stretchable strips that contain a conductive wire which deforms when the textile sensor is subjected to an externally applied force. As deformation takes place, the resistance value of the sensor changes linearly with the exerted force. The sensors as used in the present device have a certain operation range that must be taken into account while performing the measurements. Within the operation range the resistance value will change linearly with the applied external force. When the sensor is at the end of its operation range, the conductive wire is completely stretched. The resistance value will no longer change with an increasing deformation and further stretching of the sensor will result in damage.

FIG. 4 shows the device as used in the examples. Two sensor strips (left panel), which are the sensors of the axial monitoring means (1, 2), each with a different elasticity, are attached to the substrate (5) at the ends of each strip. This substrate has a very high elasticity, is very stretchable and will not exert any resistance to the erection of the penis. The sensors (1, 2) are attached to the penis through the 4 corners. These corners are sticky and not stretchable, ensuring the sensor does not move while wearing it. Two other sensor strips (right panel) are the sensors of the radial monitoring means (3, 4), also each with a different elasticity, and also attached to the substrate (5) at the ends of each strip.

In the present application, sensors with different sizes were used. A first sensor comprises strips with a length and width of 7 cm and 0.8 cm respectively, and an initial resistance of 3.5 Ohm. A second sensor comprises strips with a length and width of 2.2 cm and 0.8 cm respectively and an initial resistance of 1.4 Ohm. It is clear for a skilled person that any size of said sensors can be used, on the condition that the sizes correspond with the physiological dimensions of a human penis.

B. Artificial Penis

Figure 5:
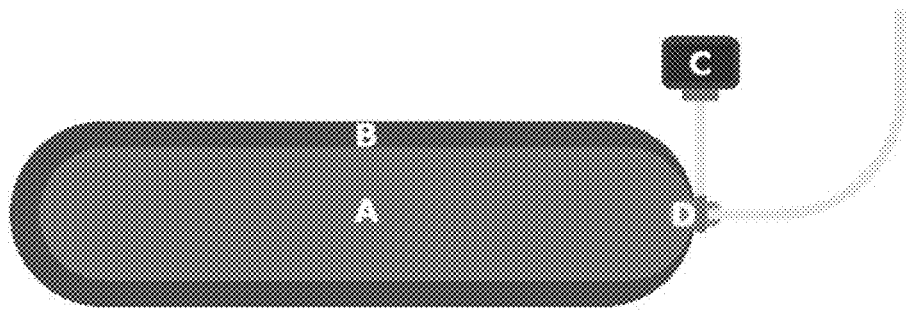

In order to perform measurements on radial and axial rigidity, an artificial penis has been developed (FIG. 5). This artificial penis was developed to mimic the working of a real penis which means that the maximum total volume of the penis is constant and cannot change within an increasing internal pressure. The internal pressure however can still increase, even when the maximum total volume of the artificial penis is reached.

Figure 6:
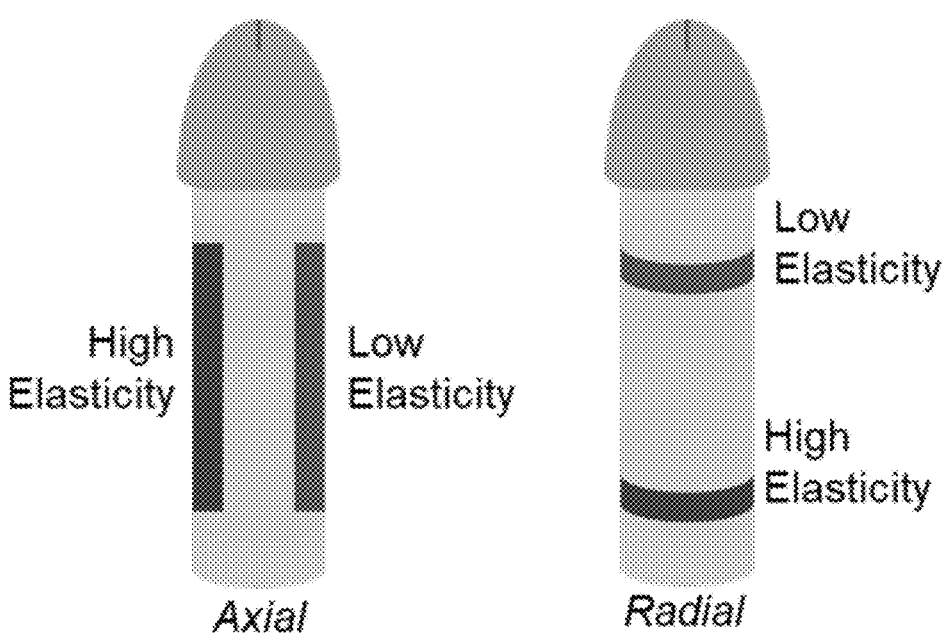
FIG. 6: Sensor placement during real-time rigidity measurements on a human penis. Sensors are placed in the axial and/or radial direction on the penis.

Before the start of the measurement, the sensor-strips are applied to the penis as shown in FIG. 6. In the present proof-of-concept study, a device was used wherein the device either comprises axial monitoring means or radial monitoring means (FIG. 6). Though, a device comprising both axial and radial monitoring means can be used as well.

The artificial penis comprises a stretchable balloon (10) and a stocking that is pulled over the balloon (11). This stocking is not stretchable and determines the maximum total volume of the penis. A pressure measurement sensor (12) is connected to the inlet (13) of the balloon. This allows the internal pressure to be monitored during the measurements. The swelling of the penis is simulated by inserting air or a liquid into the balloon.

Before performing the measurements, the sensors were first applied onto the artificial penis to evaluate whether the sensors did not experience any external influences. Then, a basic internal pressure is applied to partially swell the penis. During the measurement, a pressure pattern is applied. This pattern includes increasing the internal pressure of the artificial penis varying from the basic pressure to the maximum pressure to be applied and thus also the rigidity will change. In between measurements, the basic pressure is increased.

In a first approach, the axial rigidity was measured by erecting the artificial penis with intermediate steps (FIG. 6 left panel). The initial internal pressure was also increased with each measurement to evaluate the influence of the operation range of the sensors.

Figure 7:
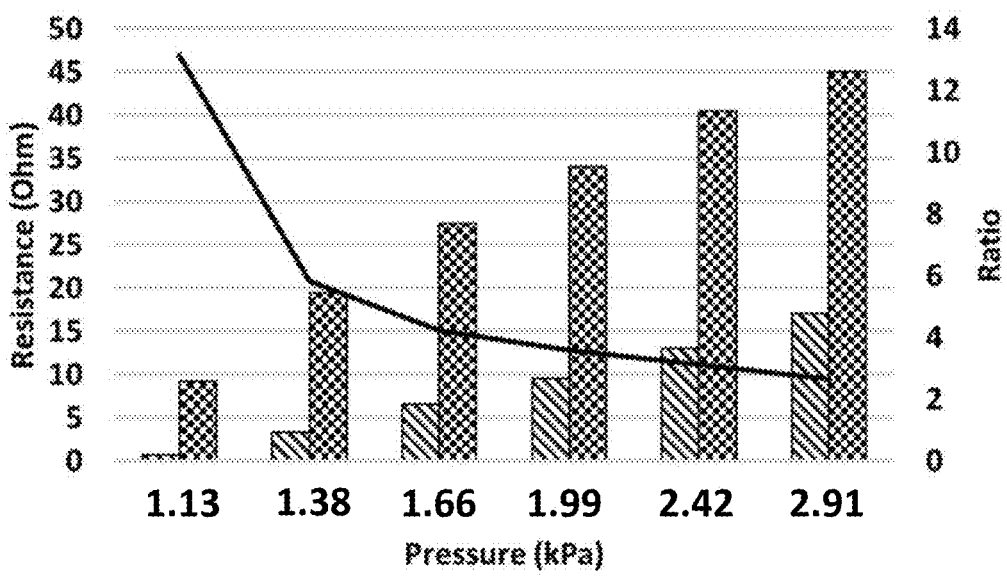
FIG. 7: Axial rigidity measurement. The resistance values increase linear with the applied pressure.

The first measurement is shown in FIG. 7. The increase in resistance is linear with the increase in pressure that was applied on the artificial penis. The sensor-strip with the lowest elasticity (E) offers the biggest resistance to deformation and will only increase as the artificial penis becomes more rigid. Further, the ratio between both sensors is decreasing as the internal pressure increases. The sensors are not saturated and did not pass the operation range.

Figure 8:
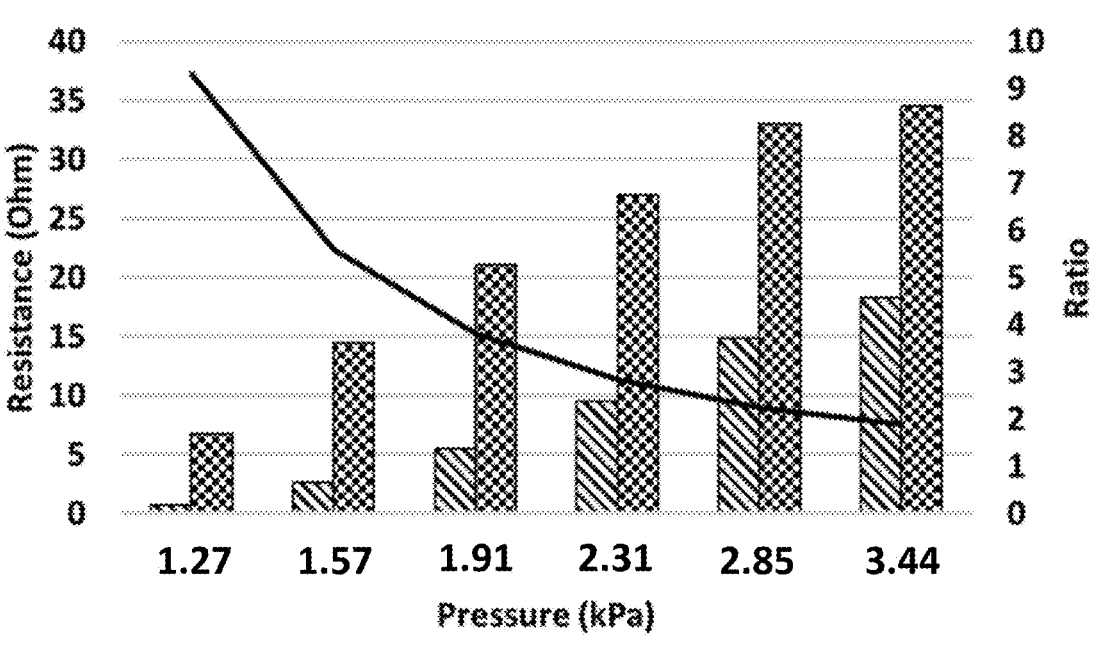
FIG. 8: Axial rigidity measurement. In the last pressure step, the strip with elasticity 2 starts to saturate.

At the start of a second measurement, the basic internal pressure was increased to 1.27 kPa. Again, and as can be observed in FIG. 8, the ratio between both sensors is decreasing as the internal pressure increases. Remarkably, for the sensor with elasticity 2, the increase in resistance is not linear anymore in the last pressure increase step. This can be explained by the fact that the sensor has reached the end of its operation range which means that a further increase in external force will not result in an increase in resistance value anymore.

Figure 9:
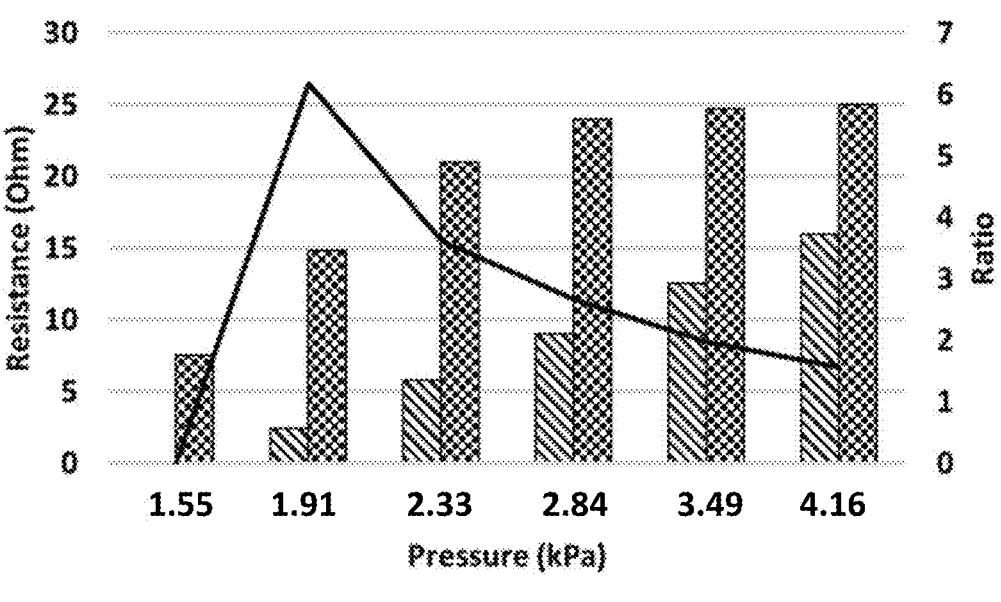
FIG. 9: Axial rigidity measurement. The sensor E2 has reached the end of its operation range and is saturated. Sensor E1 still increases linearly with increasing pressure but in the first step the pressure is not high enough for this strip to deform.

In a third measurement (FIG. 9), again the basic internal pressure was increased in the artificial penis. Here, the sensor with elasticity 2 has reached the end of its operation range, and is thus saturated. The resistance value of the sensor with elasticity 1 is still increasing win an increasing internal pressure in the artificial penis.

Figure 10:
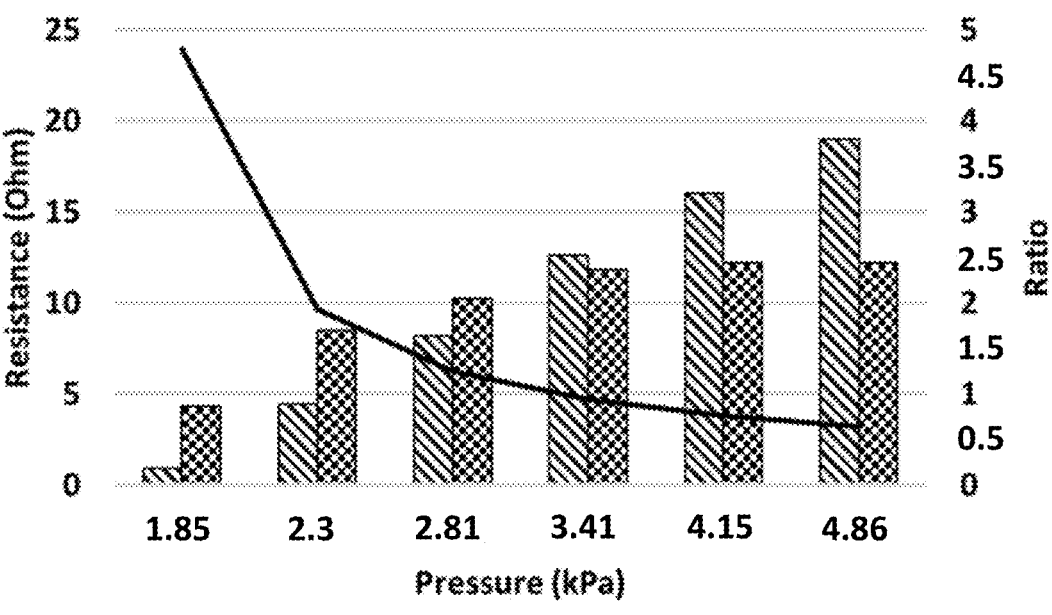
FIG. 10: Axial rigidity measurement. Sensor E2 is completely saturated and will not monitor the rigidity anymore.

The results for a last axial measurement are shown in FIG. 10. To study the effect of the operation range of the sensors, the basic internal pressure has been increased again. Now the sensor with elasticity 2 is completely saturated whilst the sensor with elasticity 1 is still measuring in its operation range.

In a second approach, the radial rigidity was measured by erecting the artificial penis with intermediate steps (FIG. 6 right panel). The measurements for the radial rigidity were performed in the same setting as the measurements for the axial rigidity.

Figure 11:
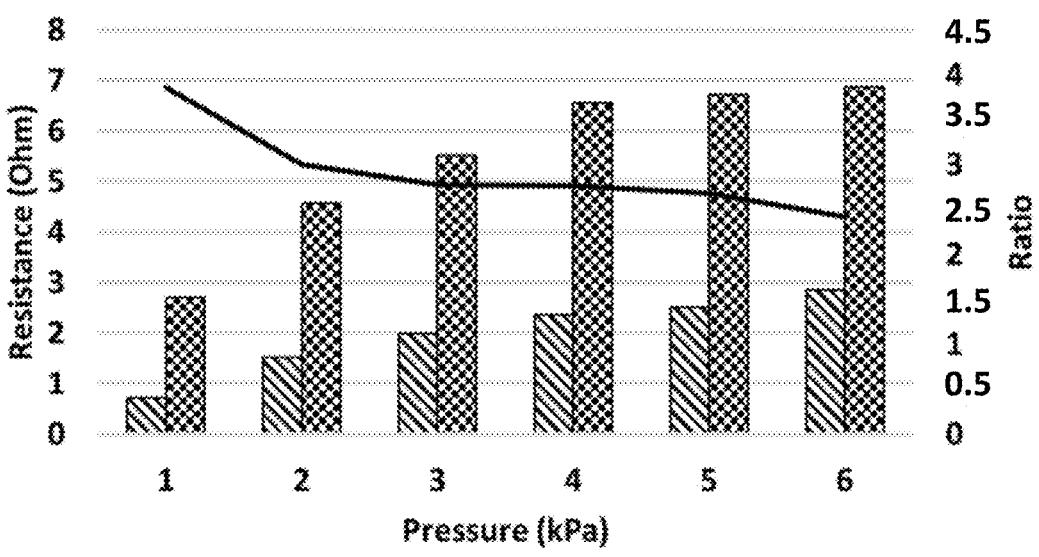
FIG. 11: Radial rigidity measurement. The sensor E2 has reached the end of its operation range and is saturated. Sensor E1 still increases linearly with increasing pressure.

In FIG. 11, the resistance increase is linear with the pressure for the first four steps. When increasing the internal pressure at step 5, the sensor with elasticity 2 becomes saturated whereas the sensor with elasticity 1 is still increasing.

C. Human Penis

Real-time measurement using the device according to the invention and as described under A, are performed on a human penis to measure the axial and/or radial rigidity.

Before the start of the measurements, the sensors of the device are applied on the penis when the penis is in a relaxed status. No external influences are exerted in the sensor-strips.

Figure 12:
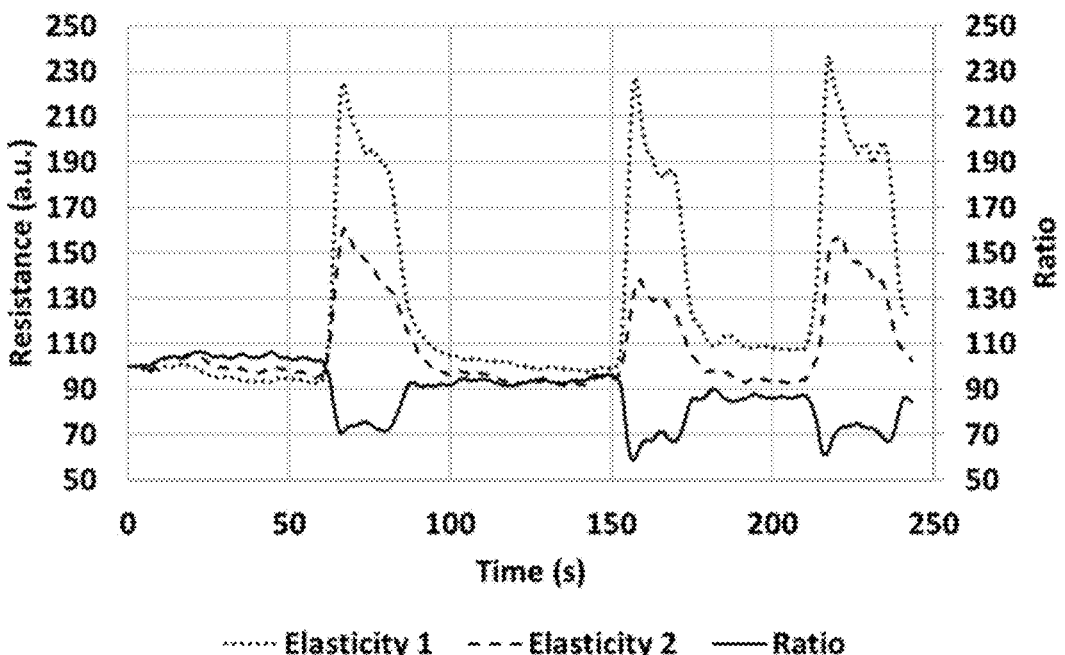
FIG. 12: Real-time measurement of axial rigidity. The erecting and relaxing penis can be observed.

The monitoring of the axial rigidity over time is shown in FIG. 12. First a reference signal was obtained by monitoring the penis in a relaxed state. Next, the erecting and relaxing penis is monitored. When the penis erects and becomes rigid, the resistance values of both sensor strips increase, and the ratio of the resistance values of both sensor-strips decreases. When the penis starts to relax, the sensor-strips shrink, resulting in a decrease of the resistance values, and an increase of the ratio, showing that the penis is not rigid anymore.

Figure 13:
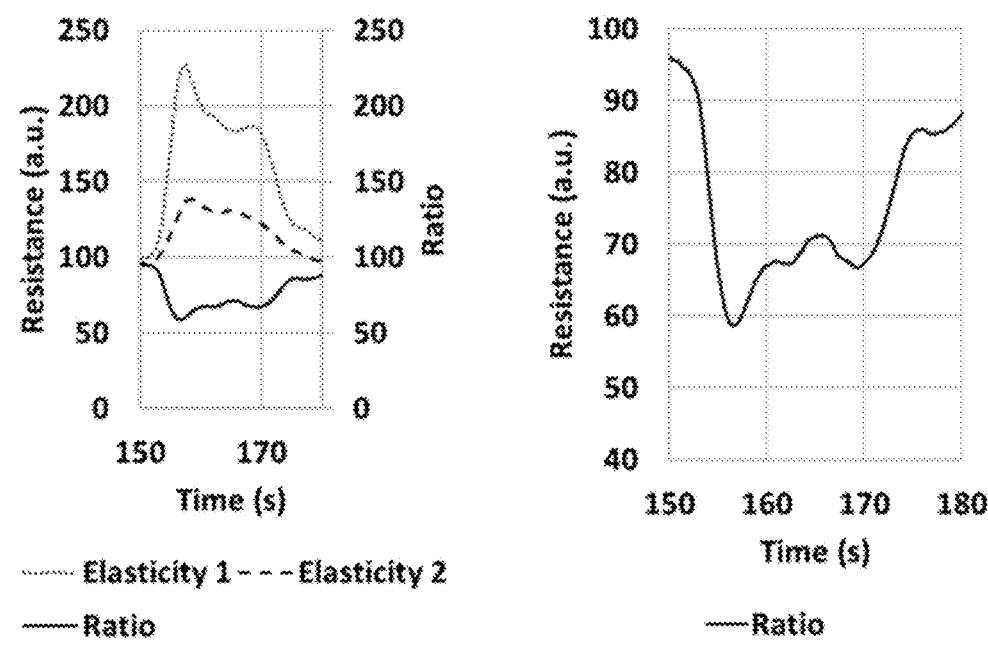
FIG. 13: An erection cycle measured for the axial rigidity. Performing linear fits on the ascending and descending edges gives information about the speed, the penis erects or relaxes.

FIG. 13 focuses on one measured erection cycle. When the detumescence takes place, the ratio of the resistance values changes. The speed of this change can also be determined, by performing a linear fit on the ascending and descending edge of the ratio (rigidity) or the strip with the highest elasticity (tumescence).

Figure 14:
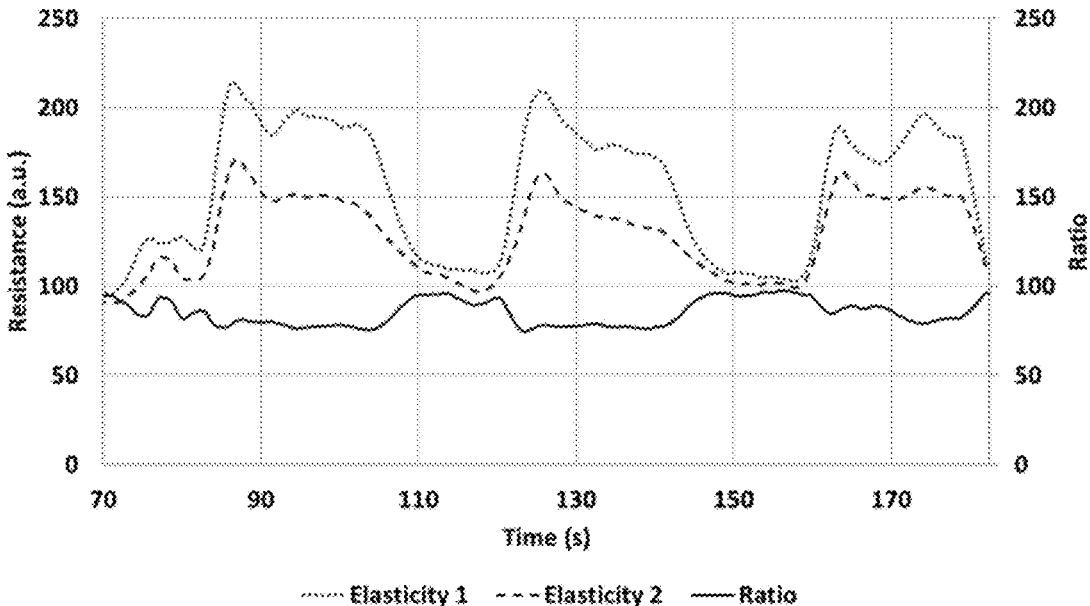
FIG. 14: Real-time measurement of radial rigidity. The erecting and relaxing of the penis can be observed.

The same measurement was repeated for the radial rigidity, with the sensor-strips placed perpendicular on the penis. In FIG. 14 the monitoring of the radial rigidity over time is shown. Again, a first reference signal was obtained by monitoring the penis in its relaxed state. Next, the erecting and relaxing of the penis is monitored. The resistance values of both sensor-strips increase when the penis erects and becomes rigid. The ratio of the resistance values of both strips then decreases. When the penis starts to relax again, the sensor-strips shrink resulting in a decrease of the resistance values, but an increase in the ratio of the resistance values, indicating that the penis is not rigid anymore.

The invention claimed is:

1. A device for measuring one or more physiological parameters of a penis, the device comprising an axial monitoring means for passively monitoring an axial rigidity of the penis, wherein the axial monitoring means comprises a first passive elastic sensor having a first elasticity and a second passive elastic sensor having a second elasticity, wherein the first elasticity and the second elasticity are different from each other, and wherein the first and second passive elastic sensors do not exert external force while measuring axial rigidity of an erection of the penis.

2. The device of claim 1, wherein the first passive elastic sensor and the second passive elastic sensor each comprise one or more semi-conductive or conductive means.

3. The device of claim 1, wherein the axial monitoring means are configured to be applied in an axial direction on the penis.

4. The device of claim 1, wherein the first passive elastic sensor and the second passive elastic sensor of the axial monitoring means are separated from one another across the width of the penis.

5. The device of claim 1, wherein the axial monitoring means further comprises a substrate with an elasticity that does not exert any resistance to an erection of the penis.

6. The device of claim 1, further comprising a radial monitoring means for passively monitoring a radial rigidity of the penis, wherein the radial monitoring means comprises a first sensor having a first elasticity and a second sensor having a second elasticity, wherein the first elasticity and the second elasticity are different from each other, and wherein the first and second sensors of the radial monitoring means do not exert external force while measuring radial rigidity of the erection of the penis.

7. The device of claim 6, wherein the radial monitoring means are configured to be applied in a radial direction around the penis.

8. The device of claim 6, wherein the first sensor and the second sensor of the radial monitoring means extend over the length of the penis.

9. The device of claim 6, wherein the first sensor and the second sensor of the radial monitoring means are separated from one another across the length of the penis.

10. The device of claim 6, wherein the first sensor and the second sensor of the radial monitoring means comprise at least one sensor at the base of the penis and at least one sensor at the tip of the penis.

11. The device of claim 6, wherein the axial monitoring means and/or the radial monitoring means further comprise a substrate with an elasticity that does not exert any resistance to the erection of the penis.

12. The device of claim 11, wherein the first sensor and the second sensor of the axial and/or radial monitoring means are attached to the substrate.

13. The device of claim 1, further comprising one or more transducers, wherein the one or more transducers convert changes in hardness and diameter of the penis into electrical signals.

14. The device of claim 1, further comprising a recorder that records electrical signals from a transducer.

15. The device of claim 1, further comprising a controller, wherein the controller is electrically connected to a transducer and controls the transducer.

16. The device according to claim 1, wherein the one or more physiological parameters are selected from the group consisting of rigidity of the penis, tumescence of the penis, hardness of the penis, diameter of the penis, growth of the penis during an erection, duration of an erection of the penis, or swelling time of the penis during an erection.

17. A method for monitoring one or more physiological parameters of a penis during a penile tumescent event with the device according to claim 1, the method comprising:
   positioning the axial monitoring means on the penis;
   optionally positioning a radial monitoring means around the penis;
   measuring resistance of the first sensor and the second sensor of the axial monitoring means and optionally the radial monitoring means during a period of time; and
   monitoring the one or more physiological parameters by measuring changes in resistance of the first sensor and the second sensor of the axial monitoring means and optionally the radial monitoring means over said period of time.

18. The method of claim 17, wherein the one or more physiological parameters are selected from the group consisting of rigidity of the penis, tumescence of the penis, hardness of the penis, diameter of the penis, growth of the penis during an erection, duration of an erection of the penis, or swelling time of the penis during an erection.

19. The device according to claim 1, wherein the first elasticity is selected to detect tumescence of the penis and the second elasticity is selected to detect rigidity of the penis.

* * * * *